US005720502A

United States Patent [19]

Cain

[11] Patent Number: 5,720,502
[45] Date of Patent: Feb. 24, 1998

[54] PAIN LOCATION AND INTENSITY COMMUNICATION APPARATUS AND METHOD

[76] Inventor: John R. Cain, 2000 SW. Fairlawn Rd., Topeka, Kans. 66604

[21] Appl. No.: 744,434

[22] Filed: Nov. 8, 1996

[51] Int. Cl.[6] ............................................. B42D 15/00
[52] U.S. Cl. ........................ 283/115; 283/70; 283/900; 434/262; 434/267
[58] Field of Search ............................... 283/67, 70, 173, 283/115, 900; 434/112, 262, 267, 270, 272, 274

[56] References Cited

U.S. PATENT DOCUMENTS

| | | |
|---|---|---|
| 3,858,351 | 1/1975 | Porter ........................ 434/267 |
| 4,165,890 | 8/1979 | Leff. | |
| 4,464,122 | 8/1984 | Fuller et al. ................. 434/262 |
| 4,561,851 | 12/1985 | Ferreira et al. ............. 434/272 |
| 4,624,642 | 11/1986 | Ferrara ........................ 434/274 |
| 4,762,494 | 8/1988 | Woods ........................ 434/270 |
| 4,795,348 | 1/1989 | Garthwaite ................. 434/112 |
| 4,865,549 | 9/1989 | Sonsteby. | |
| 4,869,531 | 9/1989 | Rees. | |
| 5,083,816 | 1/1992 | Folga et al. ................. 283/70 |
| 5,102,169 | 4/1992 | Mayfield. | |
| 5,498,034 | 3/1996 | Ford. | |

OTHER PUBLICATIONS

Microsoft Windows Solitaire Version 3.1, Dec. 1992.

*Primary Examiner*—Andrea L. Pitts
*Assistant Examiner*—Gregory Andoll
*Attorney, Agent, or Firm*—Litman, McMahon and Brown L.L.C.

[57] ABSTRACT

The present invention comprises a preprinted chart, or, in the case of software, a programmed screen display, on which is displayed front and back silhouettes of a patient. Alongside the silhouettes are provided a number of series of icons which illustrate various patient conditions, such as burn, cut, bruise, etc. with each icon series color coded to indicate pain intensity. A 24 hour row and column pain intensity time chart is provided which is also pain intensity color coded. A veterinary version of the pain intensity chart is provided for animals.

45 Claims, 4 Drawing Sheets

Fig. 1.

Patient _____
Physician _____

INSTRUCTIONS:
1. Locate pain site on body diagram.
2. Pull appropriate sticker for pain type.
3. Place sticker on pain site.
4. Green Sticker - no pain.

PAIN INTENSITY
RED - Excruciating
ORANGE - Intense
YELLOW - Discomforting
BLUE - Mild

PAIN SITE
BONE
BURN
CUT
NUMBNESS (No Feeling)
WEIGHT BEARING (AS Tolerable)
DO NOT TOUCH
PAIN
NO PAIN
PATIENT AT SLEEP
NOTHING BY MOUTH

24-HOUR PAIN INTENSITY CHART

| Hours of Day | 4 | 8 | 12 | 4 | 8 | 12 |
|---|---|---|---|---|---|---|
| 10 | | | | | | |
| 5 | | | | | | |
| 0 | | | | | | |

Notes:

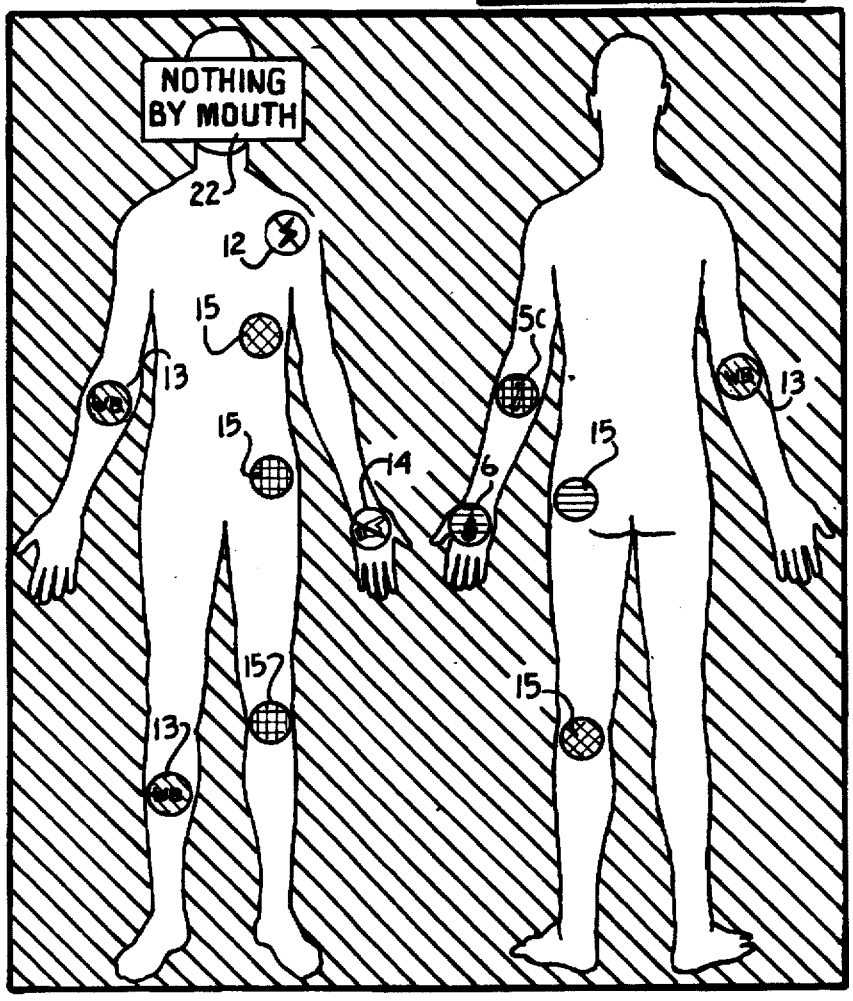
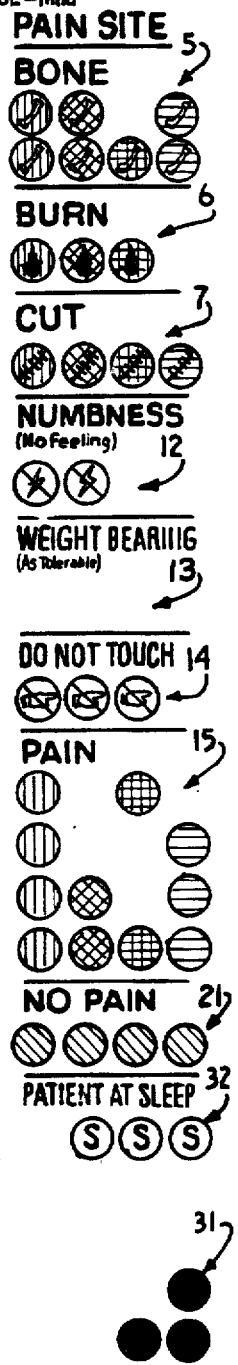
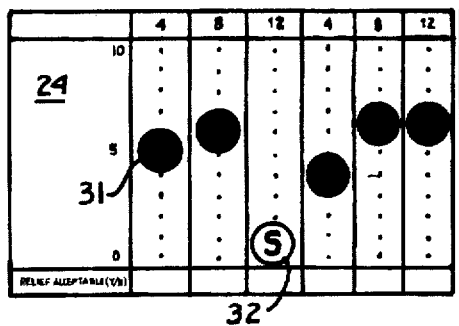

PAIN LOCATION AND INTENSITY COMMUNICATION APPARATUS AND METHOD

BACKGROUND OF THE INVENTION

1. Field of the Invention

The present invention relates generally to a pain communication apparatus and method, and, more particularly, to a patient communication system, which can be implemented as a two dimensional chart or in a software format, in which a display area including a patient silhouette is provided. A number of stickers, in the case of the hard copy embodiment, or, in the case of software, of movable icons, of varying colors are provided for attaching to the silhouette to provide instantaneous patient condition, pain location and pain intensity information.

2. Description of the Related Art

Recent trends in hospital and rehabilitation clinic patient care has seen an increasing emphasis on pain management on the part of government, insurance, and health care practitioners. Guidelines developed by the Agency for Health Care Policies and Procedures mandate better communication between patients and practitioners regarding pain. The result has been formation of QIC (Quality Inpatient Care) Pain Committees at most major hospitals. One goal of such committees has been to improve patient to care giver communication and to minimize unnecessary patient pain.

Such patient to care giver communication is problematical at best. With constant hospital shift changes, in a 24 hour period, an admitted patient will be seen by a minimum of 3 different nurses as well as nurses aids and other hospital personnel. Furthermore, a variety of physicians will typically be involved with caring for a single patient. With each new person coming into contact with the patient, information on the patient's condition must be conveyed in some fashion and charted. Frequently, this means that a sleeping patient must be awakened to answer repetitive and annoying questions. Furthermore, when a patient needs to be moved by hospital staff, the person doing the moving often does not have any idea of the patient's condition. Thus, injuries can be aggravated and/or unnecessary pain caused by hospital personnel who, often inadvertently, place weight or stress on injured limbs or other body parts.

A number of prior art attempts have been made to facilitate patient to care giver communication. For example, U.S. Pat. No. 4,165,890 to Ruth Leff, and entitled Communication Aid, is drawn to a series of cards attached to a ring for use by a patient with limited communication ability. Each card communicates a physical need or condition, such as wheelchair, stomach ache, etc. to a second party such as a nurse, nurse's aid, etc.

In U.S. Pat. No. 4,865,549 to Kristi Sonsteby, and entitled Medical Documentation and Assessment Apparatus, a number of modularized packets are color coded to represent different anatomical features of a patient, such as cardiovascular, neurological, etc. Matching diagnostic sheets are provided within each packet to place in a patient's file or chart.

In U.S. Pat. No. 4,869,531 to Michael Rees, and entitled Apparatus and Method for Documenting Physical Examinations, a group of pre-printed anatomical stickers are provided upon which an examining physician can directly mark the location, size, shape, etc. of any abnormality.

In U.S. Pat. No. 5,102,169 to Mary Mayfield, and entitled Medication Management System, a number of medications are listed on a time chart and color and shape coded stickers are associated with each medicine on the chart and are attached to the medicine containers as well.

In U.S. Pat. No. 5,498,034 to Betheline Ford, and entitled Patient Care Information System, a photograph of a patient's face is positioned on a chart and any number of patient care icons are positioned proximate the photograph to designate sensory losses, mobility limitations, safety concerns, etc. The photograph is apparently used only for positive identification.

Interestingly, none of these prior art patents is concerned with the communication of the pain causing condition, pain location and pain intensity to an attending care provider.

Accordingly, it is clear then, that a need exists for a reliable, practical and inexpensive apparatus and method which permits a patient or a patient attendant to quickly, effectively and accurately communicate pain location and intensity to an attending care provider. The present invention addresses this problem.

SUMMARY OF THE INVENTION

The present invention comprises a preprinted two dimensional chart, or, in the case of software, a programmed screen display, on which is displayed front and back silhouettes of a patient. Alongside the silhouettes are provided a number of series of icons which illustrate various patient conditions, such as burn, cut, bruise, etc. Each icon series is color coded, e.g. from blue to yellow to orange to red to indicate pain intensity with blue being minimal and red being maximum pain. In addition, a number of icons, which may be green, are provided to indicate areas of no pain and/or "weight bearing" body areas capable of sustaining weight or handling stress with minimal or no pain. Finally, a row and column 24 hour pain intensity time chart is provided on which color coded icons indicating the degree of overall pain can be positioned periodically, on a four hour cycle. A veterinary version of the pain intensity chart is provided for animals.

OBJECTS AND ADVANTAGES OF THE INVENTION

The principle objects and advantages of the present invention include: providing a patient pain communication apparatus and method; providing such an apparatus and method which reliably, quickly and effectively communicates pain sources, pain location and pain intensity from a patient to a health care provider; providing such an apparatus and method in which a patient silhouette is provided on a chart, either in hard copy or on a computer screen display; providing such an apparatus and method in which a number of informational icons are provided for localized attachment to the silhouette with each icon being color coded for pain intensity; providing such an apparatus and method which includes a pain intensity time chart for periodic updating by health care personnel; providing a veterinary version of the pain chart for use with animals; and providing such an apparatus and method which is economical to manufacture, efficient in operation, and which is particularly well adapted for the proposed usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an illustration of a patient pain location and intensity chart and associated color coded icon stickers.

FIG. 2 is an illustration of the chart of FIG. 1 in use by a particular patient to communicate pain location and intensity to an attending health care provider.

FIG. 3 is an illustration of a software screen display version of the patient pain intensity and location communication apparatus.

DETAILED DESCRIPTION OF THE PREFERRED EMBODIMENTS

I. Introduction and Environment

Figure 4:
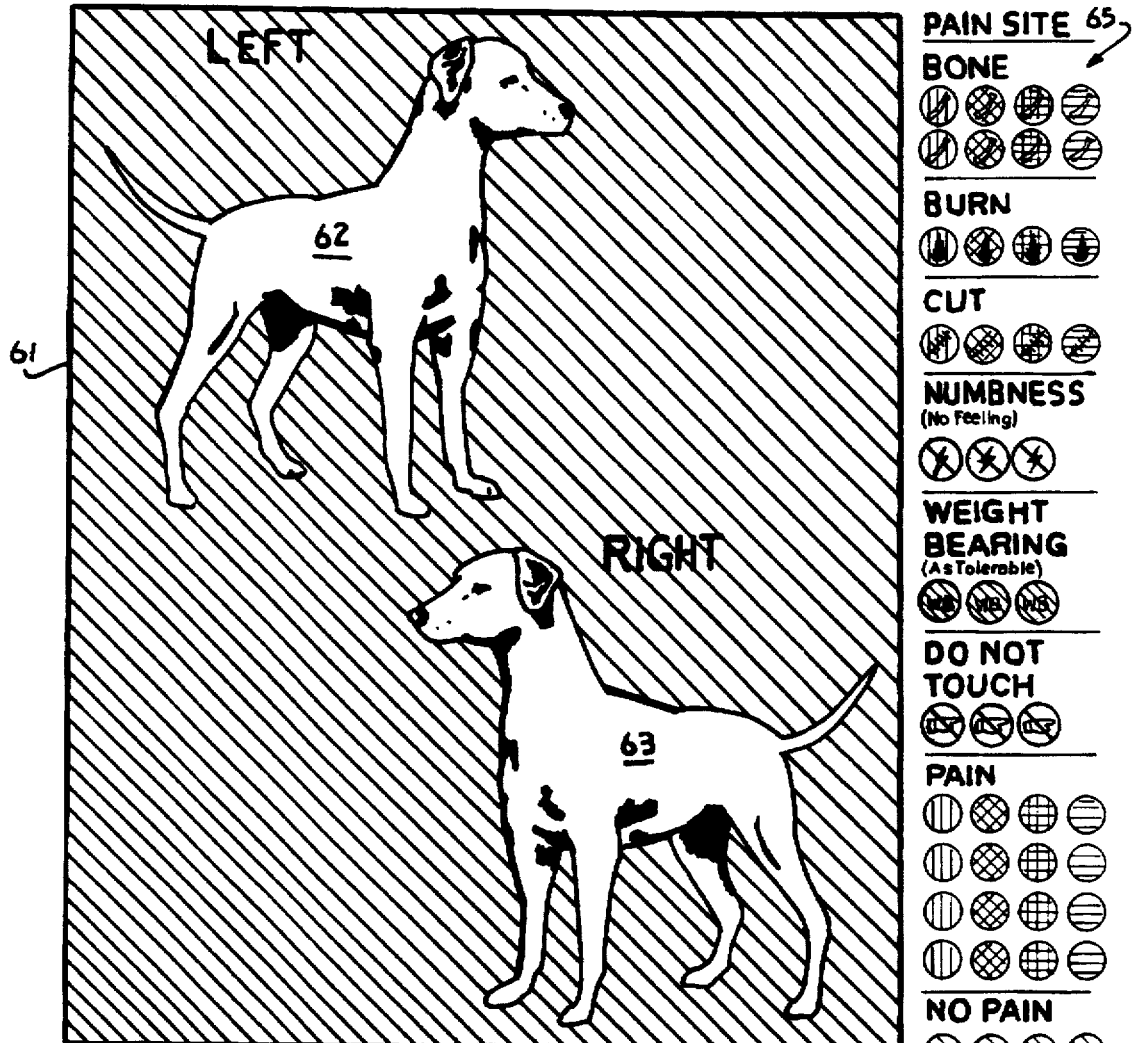
FIG. 4 is an illustration of a veterinary version of the pain intensity and location communication apparatus.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "up", "down", "right" and "left" will refer to directions in the drawings to which reference is made. Said terminology will include the words specifically mentioned, derivatives thereof and words of a similar import.

Referring to the drawings in more detail, reference numeral 1 in FIG. 1 generally designates a patient pain intensity and location communication apparatus in the form of a hard copy two dimensional chart including front and back patient silhouettes 2 and 3, respectively, displayed on a colored background in a first display area 4. A plurality of pain source icon groups 5, 6, and 7 are positioned alongside the background 4 in a second display area 8. The icon group 5 indicates a broken bone, the icon group 6 indicates a burn, and the icon group 7 indicates a cut. Each of the icon groups 5–7 is formed by a series of stickers which can be removed from the icon location and placed on the silhouettes in particular locations to indicate pain location. Meanwhile, the icon groups 5–7 are color coded to represent pain intensity, as described in a pain intensity color code guide 11. For example, the broken bone icon group 5 includes a number of stickers 5a, 5b, 5c and 5d with the sticker 5a being blue in color, the sticker 5b being yellow in color, the sticker 5c being orange in color and the sticker 5d being red in color. Thus, from left to right, the stickers 5a to 5d represent increasing pain intensity, as described in the color code guide 11. The icon groups 6 and 7 are similarly color coded. A patient or a person attending the patient can thus select a particular color of icon indicating a particular condition and intensity of pain, remove the icon sticker and place it on the appropriate silhouette 2 or 3, as shown in FIG. 2.

Referring again to FIG. 1, a number of additional icon groups are provided, each including a plurality of stickers. For example, an icon group 12 includes stickers indicating numbness or lack of feeling; an icon group 13 includes stickers indicating weight bearing areas or areas of the patient's body which are capable of supporting weight or of being handled by personnel without intolerable pain; an icon group 14 indicates areas of intense pain or areas which should not be touched; an icon group 15 indicates areas of pain without a specific cause, with the icons within the group 15 being color coded dots, again as indicated in the guide 11; an icon group 21 includes dots indicating areas of no pain, which dots can be of a uniform color different than the colors in the guide 11, e.g. green; and a sticker 22 indicating nothing by mouth to prevent any foods, liquids or medicine to be administered orally can be prominently placed over the mouth of the silhouette 2.

A third display area 23 includes a row and column overall pain intensity indicator chart 24. In the chart 24, column divisions 25 indicate a time line, such as four hour windows in a 24 hour day. Row divisions 26 represent overall pain intensity on a scale from 0 being non-existent or minimal to 10 being maximum. In the second display area 8, an icon group 31 includes stickers of a different color, e.g. black, which can be adhered to the chart 24 in the appropriate time column at the appropriate pain level to keep a running chart of overall pain. An icon group 32 includes stickers labeled as "S" to indicate that the patient was asleep during the monitoring period. This might indicate to personnel to wake the patient during the next monitoring period.

An indicia display area 33 provides an area for patient and physician identification, an area 34 is provided with instructions on use of the chart 1 and an area 35 is provided for miscellaneous notes.

Referring to FIG. 2, an example is provided of the chart 1 in use for a patient with extensive injuries on the left side of his body. For example, an orange sticker 5c indicating an intensely painful broken bone is attached to his left arm; a red burn icon sticker 6 and a "Do Not Touch" icon sticker 14 are attached to his left hand; a numbness icon sticker 12 is attached to his left shoulder; a number of pain stickers 15, which can be of varying pain intensity color codes, are distributed over several portions of the left side of his body; and the "nothing by mouth" sticker 22 is attached over his mouth. By contrast, on both sides of his right arm, as well as his right leg, weight bearing stickers 13 are attached to indicate that these are areas which can support weight with tolerable or no pain.

Still referring to FIG. 2, the row and column pain intensity chart 24 includes a number of stickers 31 placed in five of the six time columns 26. The stickers 31 are positioned to indicate pain intensities from 3 to 6 on a scale of 10. In addition, a sticker 32 is positioned in one of the time columns to indicate that the patient was sleeping during that monitoring period.

Figure 3:
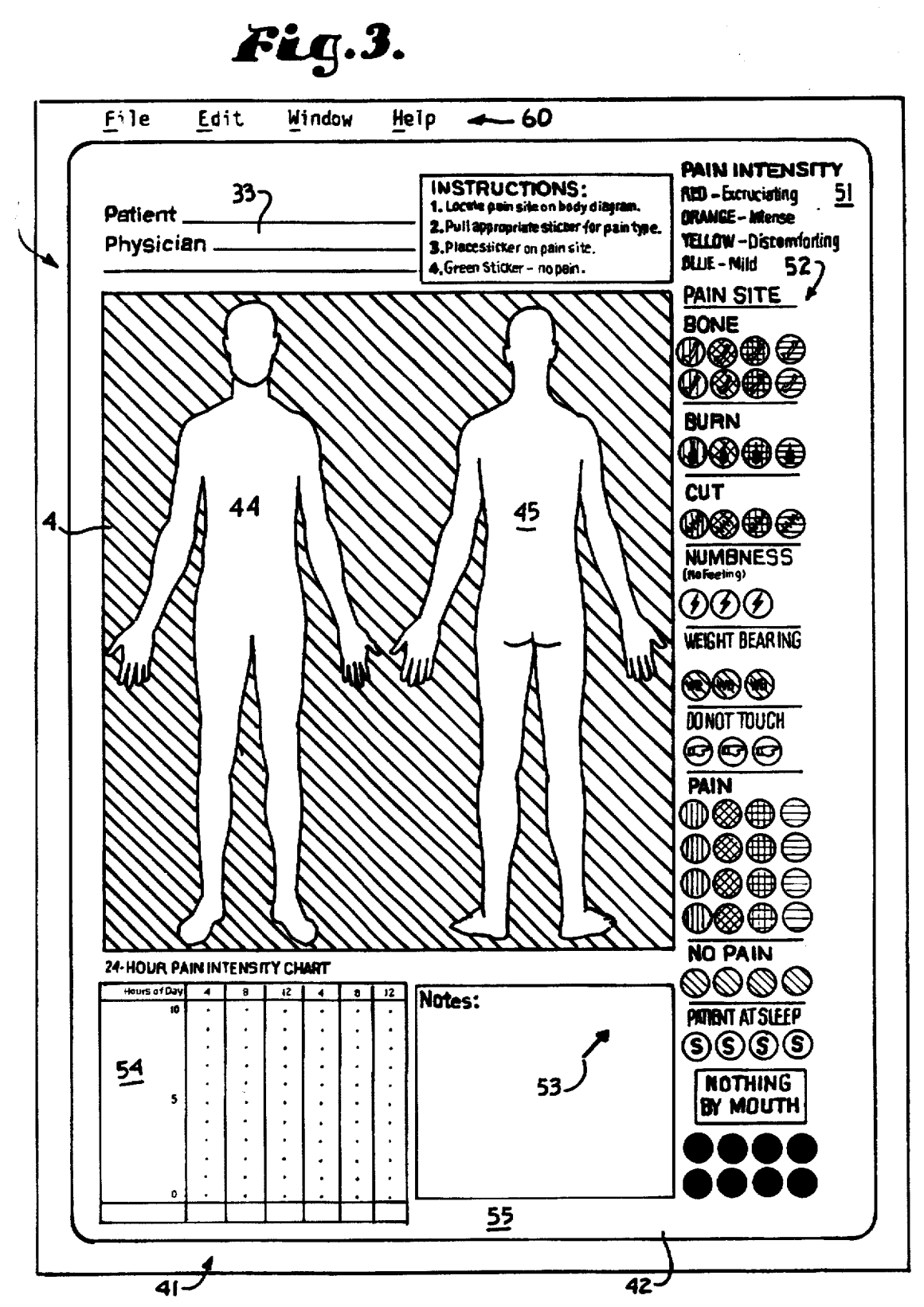

Referring to FIG. 3, a computer controlled screen display 41 is programmed to electronically display a chart 42 which is essentially identical in detail to the hard copy chart 1 of FIGS. 1 and 2. The electronic chart 42 includes a first display area 43 with a pair of body silhouettes 44 and 45. A second display area 51 includes a number of color coded icons 52 which are identical in meaning to the icon groups 5–7, 12–15, 21, 22, 31 and 32 of FIGS. 1 and 2, and which will not be further described. These icons are selectable via a standard "point and click" method such that they can be dragged from the second display area 51 onto the silhouettes 44 and 45 in the first display area 43 via a cursor 53 and mouse (not shown), or onto a row and column overall pain intensity chart 54 in a third display area 55, as described above with reference to FIGS. 1 and 2. A typical pull down menu 60 is provided above the screen display areas 43 and 51 which pull down menu 60 allows each chart 42 to be stored as a separate graphics file and/or printed in a known manner.

Referring to FIG. 4, a veterinary version of the invention is illustrated. The veterinary version, which can also be implemented as hard copy charts or computerized graphical screen displays, includes a first display area 61 with left and right animal silhouettes 62 and 63, respectively. A second display area 64 includes a number of color coded icon groups, generally indicated at 65. The icon groups 65, again, are essentially identical in form and function to those illustrated in FIGS. 1–3, with the exception of icon groups 31 and 32, which are not used in the veterinary version, and will not be further described herein. Additional icon groups which are specially tailored to veterinary use, such as "Fat Deposits" icons 71, can be provided as well. Instead of a row and column time overall pain intensity chart, which, of course, would be relatively useless with an animal patient incapable of self evaluation, a special instructions window 72 is provided for specific operations, such as feeding, wound dressing and bathing, etc.

It should be noted that the charts and screen displays illustrated in FIGS. 1–4 and described herein are exemplary only and that many other variations can be devised. For example, the illustrated silhouettes 2 and 3 represent an adult male, but it is contemplated that other charts with representations of an adult female or male or female children can be used. The icon groupings are also not limited to those shown, but can include other symbols, such as bruises, abrasions, heart disease, puncture wounds, etc. In the veterinary version, a silhouette of a dog is illustrated as representative, but other versions including cats, horses and other domestic animals and pets are contemplated. The colors used in the pain intensity and other color coding are also representative only, since many other color schemes can be used, although the gradations from blue to red are somewhat accepted in the field.

It is thus to be understood that while certain forms of the present invention have been illustrated and described herein, it is not to be limited to the specific forms or arrangement of parts described and shown.

What is claimed and desired to be secured by Letters Patent is as follows:

1. A patient pain communication apparatus comprising:
   a) a graphic display medium including:
      i) a first display area including at least one graphic image representing a portion of a body;
      ii) a second display area including a plurality of icons representing particular patient pain conditions, at least some of said icons including coding to represent pain intensity; and wherein
      iii) said icons are movable from said second display area to said first display area such that they can be positioned on said body graphic image to indicate either pain location or both pain location and intensity.

2. A patient pain communication apparatus as in claim 1, wherein said icon coding is color coding with different colors representing different pain intensities.

3. A patient pain communication apparatus as in claim 1, wherein said plurality of icons includes some icons which incorporate information on injury types.

4. A patient pain communication apparatus as in claim 3, wherein said injury types include one or more of the following:
   a) broken bones;
   b) burns;
   c) cuts; and
   d) numbness.

5. A patient pain communication apparatus as in claim 1, and further including movable icon(s) which incorporate information on areas which are weight bearing.

6. A patient pain communication apparatus as in claim 1, wherein said plurality of icons includes icon(s) which incorporate information on areas which should not be touched.

7. A patient pain communication apparatus, comprising:
   a) a graphic display medium including:
      i) a first display area including at least one graphic image representing a portion of a body;
      ii) a second display area including a plurality of icons representing particular patient pain conditions;
      iii) a third display area including a time based pain intensity chart; and wherein
      iv) said icons are movable from said second display area to said first display area such that they can be positioned on said body graphic image to indicate pain location.

8. A patient pain communication apparatus as in claim 7, said time based pain intensity chart including a row and column matrix with a time scale represented on either the row or column and a pain intensity scale being represented on the remaining one of the row and column.

9. A patient pain communication apparatus as in claim 8, wherein said plurality of icons includes icon(s) which incorporate information on pain intensity, said pain intensity icons being movable to said row and column matrix.

10. A patient pain communication apparatus as in claim 8, and further including icon(s) which indicate a sleeping patient, said sleeping patient icons being movable to said row and column matrix.

11. A patient pain communication apparatus as in claim 1, and further including movable icon(s) which incorporate information on areas which are experiencing no pain.

12. A patient pain communication apparatus as in claim 1, wherein said graphics display area comprises a two dimensional chart and said icons comprise removable and replaceable stickers.

13. A patient pain communication apparatus as in claim 1, wherein said graphics display area comprises a computer screen and said icons are computer graphics which are selectable and movable via a "point, click and drag" cursor method.

14. A patient pain communication apparatus as in claim 1, wherein said apparatus is designed for human patient use and where said at least one graphic image representing a portion of a body represents a portion of a human body.

15. A patient pain communication apparatus as in claim 14, wherein there are two of said graphic images representing a portion of a body with a first of said graphic images representing a front silhouette and the second of said graphic images representing a rear silhouette.

16. A patient pain communication apparatus as in claim 1, wherein said apparatus is designed for veterinary patient use and where said at least one graphic image representing a portion of a body represents a portion of an animal body.

17. A patient pain communication apparatus as in claim 16, wherein there are two of said graphic images representing a portion of a body with a first of said graphic images representing a left side silhouette and the second of said graphic images representing a right side silhouette.

18. A patient pain communication apparatus comprising:
   a) a graphic display medium including a computer screen driven by a programmed computer, said display mediums including:
      i) a first display area including at least one graphic image representing a portion of a body;

ii) a second display area including a plurality of icons representing particular patient pain conditions with at least some of said icons including coding representing pain intensity, said icons being computer graphics which are selectable and movable via a "point, click and drag" cursor method such that they are movable from said second display area to said first display area such that they can be positioned on said body graphic image to indicate pain location.

19. A patient pain communication apparatus as in claim 18, wherein said icon pain intensity coding is color coding with different colors representing different pain intensities.

20. A patient pain communication apparatus as in claim 18, wherein said plurality of icons includes some icons which incorporate information on injury types.

21. A patient pain communication apparatus as in claim 20, wherein said injury types include one or more of the following:
    a) broken bones;
    b) burns;
    c) cuts; and
    d) numbness.

22. A patient pain communication apparatus as in claim 18, and further including movable icon(s) which incorporate information on areas which are weight bearing.

23. A patient pain communication apparatus as in claim 18, wherein said plurality of icons includes icon(s) which incorporate information on areas which should not be touched.

24. A patient pain communication apparatus, comprising:
    a) a graphic display medium including a computer screen driven by a programmed computer, said display mediums including:
        i) a first display area including at least one graphic image representing a portion of a body;
        ii) a second display area including a plurality of icons representing particular patient pain conditions with at least some of said icons including coding representing pain intensity, said icons being computer graphics which are selectable and movable via a "point, click and drag" cursor method such that they are movable from said second display area to said first display area such that they can be positioned on said body graphic image to indicate pain location; and
        iii) a third display area including a time based pain intensity chart.

25. A patient pain communication apparatus as in claim 24, said time based pain intensity chart including a row and column matrix with a time scale represented on either the row or column and a pain intensity scale being represented on the remaining one of the row and column.

26. A patient pain communication apparatus as in claim 26, and further including icon(s) which indicate a sleeping patient, said sleeping patient icons being movable to said row and column matrix.

27. A patient pain communication apparatus as in claim 25, wherein said plurality of icons includes icon(s) which incorporate information on areas which are experiencing no pain.

28. A patient pain communication apparatus as in claim 18, wherein said apparatus is designed for human patient use and where said at least one graphic image representing a portion of a body represents a portion of a human body.

29. A patient pain communication apparatus as in claim 28, wherein there are two of said graphic images representing a portion of a body with a first of said graphic images representing a front silhouette and the second of said graphic images representing a rear silhouette.

30. A patient pain communication apparatus as in claim 18, wherein said apparatus is designed for veterinary patient use and where said at least one graphic image representing a portion of a body represents a portion of an animal body.

31. A patient pain communication apparatus as in claim 30, wherein there are two of said graphic images representing a portion of a body with a first of said graphic images representing a left side silhouette and the second of said graphic images representing a right side silhouette.

32. A patient pain communication apparatus comprising:
    a) a graphic display medium including a two dimensional chart comprising:
        i) a first display area including at least one graphic image representing a portion of a body;
        ii) a second display area including a plurality of icons representing particular patient pain conditions with at least some of said icons including coding representing pain intensity, said icons being removable and replaceable stickers which can be removed from said second display area and attached to said first display area such that they can be positioned on said body graphic image to indicate either pain location or both pain location and intensity.

33. A patient pain communication apparatus as in claim 32, wherein said icon pain intensity coding is color coding with different colors representing different pain intensities.

34. A patient pain communication apparatus as in claim 32, wherein said plurality of icons includes some icons which incorporate information on injury types.

35. A patient pain communication apparatus as in claim 34, wherein said injury types include one or more of the following:
    a) broken bones;
    b) burns;
    c) cuts; and
    d) numbness.

36. A patient pain communication apparatus as in claim 34, and further including removable and replaceable sticker icon(s) which incorporate information on areas which are weight bearing.

37. A patient pain communication apparatus as in claim 32, wherein said plurality of icons includes icon(s) which incorporate information on areas which should not be touched.

38. A patient pain communication, comprising:
    a) a graphic display medium including a two dimensional chart comprising:
        i) a first display area including at least one graphic image representing a portion of a body;
        ii) a second display area including a plurality of icons representing particular patient pain conditions with at least some of said icons including coding representing pain intensity, said icons being removable and replaceable stickers which can be removed from said second display area and attached to said first display area such that they can be positioned on said body graphic image to indicate either pain location or pain location and intensity; and
        iii) a third display area including a time based pain intensity chart.

39. A patient pain communication apparatus as in claim 38, said time based pain intensity chart including a row and column matrix with a time scale represented on either the row or column and a pain intensity scale being represented on the remaining one of the row and column.

40. A patient pain communication apparatus as in claim 41, and further including removable and replaceable sticker icon(s) which indicate a sleeping patient, said sleeping patient icons being movable to said row and column matrix.

41. A patient pain communication apparatus as in claim 41, and further including removable and replaceable sticker icon(s) which incorporate information on areas which are experiencing no pain.

42. A patient pain communication apparatus as in claim 32, wherein said apparatus is designed for human patient use and where said at least one graphic image representing a portion of a body represents a portion of a human body.

43. A patient pain communication apparatus as in claim 42, wherein there are two of said graphic images representing a portion of a body with a first of said graphic images representing a front silhouette and the second of said graphic images representing a rear silhouette.

44. A patient pain communication apparatus as in claim 32, wherein said apparatus is designed for veterinary patient use and where said at least one graphic image representing a portion of a body represents a portion of an animal body.

45. A patient pain communication apparatus as in claim 44, wherein there are two of said graphic images representing a portion of a body with a first of said graphic images representing a left side silhouette and the second of said graphic images representing a right side silhouette.

* * * * *